(12) United States Patent
Feustel et al.

(10) Patent No.: US 8,388,606 B2
(45) Date of Patent: Mar. 5, 2013

(54) LOCKING MECHANISM

(75) Inventors: Aaron Feustel, Claremont, NH (US);
Frank Lopez, Claremont, NH (US);
Bradley Bender, Lincoln, RI (US);
Ronald Rudowsky, Plymouth, MA (US)

(73) Assignee: Bradley Bender, Lincoln, RI (US)

( * ) Notice: Subject to any disclaimer, the term of this patent is extended or adjusted under 35 U.S.C. 154(b) by 0 days.

(21) Appl. No.: 13/410,822

(22) Filed: Mar. 2, 2012

(65) Prior Publication Data

US 2012/0232532 A1  Sep. 13, 2012

Related U.S. Application Data

(60) Provisional application No. 61/464,938, filed on Mar. 10, 2011.

(51) Int. Cl.
*A61B 17/00* (2006.01)
*F16B 17/00* (2006.01)
(52) U.S. Cl. ........................................... 606/1; 403/345
(58) Field of Classification Search .................. None
See application file for complete search history.

(56) References Cited

U.S. PATENT DOCUMENTS

| 5,127,915 | A | * | 7/1992 | Mattson ..................... 606/120 |
| 5,653,729 | A | | 8/1997 | Chappuis et al. |
| 6,592,603 | B2 | | 7/2003 | Lasner |
| 2004/0254604 | A1 | | 12/2004 | Viart et al. |
| 2007/0027474 | A1 | | 2/2007 | Lasner |

OTHER PUBLICATIONS

International Search Report and Written Opinion in corresponding PCT/US2012/028206 dated Sep. 25, 2012.

* cited by examiner

*Primary Examiner* — Henry M Johnson, III
*Assistant Examiner* — Scott T Luan
(74) *Attorney, Agent, or Firm* — Sughrue Mion, PLLC

(57) ABSTRACT

Provided herein are a locking mechanism including a male extension including a straight portion and a graduated step portion; and a female extension configured to receive the male extension, and including a pair of protruding tabs, which are spaced apart to allow the straight portion of the male extension to pass through a space between the protruding tabs, and which contact the graduated step portion if the male extension is inserted a first predetermined distance into the female extension.

18 Claims, 12 Drawing Sheets

LOCKING MECHANISM

CROSS-REFERENCE TO RELATED APPLICATION

This application claims priority from U.S. Provisional Application No. 61/464,938, filed on Mar. 10, 2011, in the U.S. Patent and Trademark Office the disclosure of which is incorporated herein by reference in its entirety.

BACKGROUND

Apparatuses consistent with exemplary embodiments relate to a locking mechanism for a surgical instrument.

Related art precision surgical instruments, such as surgical scissors, forceps, hemostats, etc., may include a locking mechanism on the handle so as to secure the instrument in a fixed position. For example, hemostats and forceps typically have a locking mechanism including a series of interlocking teeth, with several teeth on each handle. When pushed together, the teeth interlock, allowing a user to adjust the instrument to a desired degree of clamping force.

However, there are drawbacks with the related art locking mechanisms. For example, precision locking mechanisms are difficult and costly to manufacture. Additionally, many related art locking mechanisms have been found to bend or fail frequently.

Other instruments may lack a suitable locking mechanism altogether. For example, U.S. Pat. No. 6,592,603 ("the '603 patent" hereinafter), which is incorporated herein by reference, discloses in FIGS. 1, 2 and 4, a pair of surgical forceps that include spring arms connected to handle portions of the forceps. However, the forceps of the '603 patent do not include any locking mechanism at all. Consequently it is difficult to secure the instrument in a fixed position.

In view of such shortcomings, it is clear that better solutions are needed.

SUMMARY

One or more exemplary embodiments may overcome the above disadvantages and other disadvantages not described above. However, it is understood that one or more exemplary embodiment are not required to overcome the disadvantages described above, and may not overcome any of the problems described above.

An aspect of an exemplary embodiment provides a locking mechanism including: a male extension including a straight portion and a graduated step portion; and a female extension configured to receive the male extension, and including a pair of protruding tabs, which are spaced apart to allow the straight portion of the male extension to pass through a space between the protruding tabs, and which contact the graduated step portion if the male extension is inserted a first predetermined distance into the female extension.

As the male side is urged toward the female side, the straight portion of the male extension may be formed to pass through the space between the protruding tabs, and the pair of protruding tabs may contact respective left and right front flat surfaces of the female extension.

The female extension may further include a pair of U-shaped sections which oppose each other.

Upper portions of the pair of U-shaped sections respectively include the pair of protruding tabs, and wherein lower portions of the pair of U-shaped sections respectively include left and right front flat surfaces of the female extension.

The opposing U-shaped sections may define a channel section into which the straight portion of the male extension is insertable.

The graduated step portion of the male extension may include an outermost pair of protruding tabs and an innermost pair of protruding tabs, the outermost protruding tabs being configured to contact the left and right front flat surfaces of the female extension if the male extension is inserted the first predetermined distance into the female extension.

The outermost pair of protruding tabs may respectively contact the left and right front flat surfaces of the female extension in respective areas on the and right front flat surfaces of the female extension below the pair of protruding tabs of the female extension.

The innermost pair of protruding tabs of the graduated step portion of the male extension may fit within a space between the left and right front flat surfaces of the female extension and under the protruding tabs of the female extension.

A top surface of each of the innermost pair of protruding tabs of the graduated step portion of the male extension may contact respective bottom surfaces of the pair of protruding tabs of the female extension if the male extension is inserted the first predetermined distance into the female extension.

If the male extension is inserted the first predetermined distance into the female extension, the locking mechanism may then be in a locked state where the male side is prevented from moving away from the female side.

If a gap exists between the male extension and the female extension, the locking mechanism may then be in a free state where the male side is moveable in a direction away from the female side.

If the male side is urged toward the female side a second predetermined distance beyond the first predetermined distance, the locking mechanism may be moveable from the locked state to the free state.

The female extension may further include a pair of U-shaped sections which oppose each other, and the opposing U-shaped sections define a channel section into which the straight portion of the male extension is insertable as the male side is urged toward the female side moving from the free state to the locked state.

The graduated step portion of the male extension may include an outermost pair of protruding tabs and an innermost pair of protruding tabs, the outermost protruding tabs being configured to contact left and right front flat surfaces of the female extension if the male extension is inserted the first predetermined distance into the female extension, and the channel section may accommodate the outermost pair of protruding tabs of the graduated step portion as the male side is urged toward the female side beyond the second predetermined distance and the locking mechanism moves from the locked state back to the free state.

An aspect of an exemplary embodiment provides an instrument having a first handle portion and a second handle portion, the instrument comprising a locking mechanism including: a male extension including a straight portion and a graduated step portion; and a female extension configured to receive the male extension, and including a pair of protruding tabs, which are spaced apart to allow the straight portion of the male extension to pass through a space between the protruding tabs, and which contact the graduated step portion if the male extension is inserted a first predetermined distance into the female extension, wherein the male extension is connected to the first handle portion and the female extension is connected to the second handle portion.

The instrument may be a surgical instrument having a proximal end and a distal end, the proximal end being toward a working portion of the surgical instrument, and the distal end being further away from the working portion of the surgical instrument than the proximal end.

The locking mechanism may be located closer to the distal end than the proximal end of the surgical instrument.

The surgical instrument may be a pair of forceps or a pair of surgical scissors.

BRIEF DESCRIPTION OF THE DRAWINGS

The above and/or other aspects will be more apparent by describing in detail exemplary embodiments, with reference to the accompanying drawings, in which.

DETAILED DESCRIPTION OF THE EXEMPLARY EMBODIMENTS

Figure 1A:
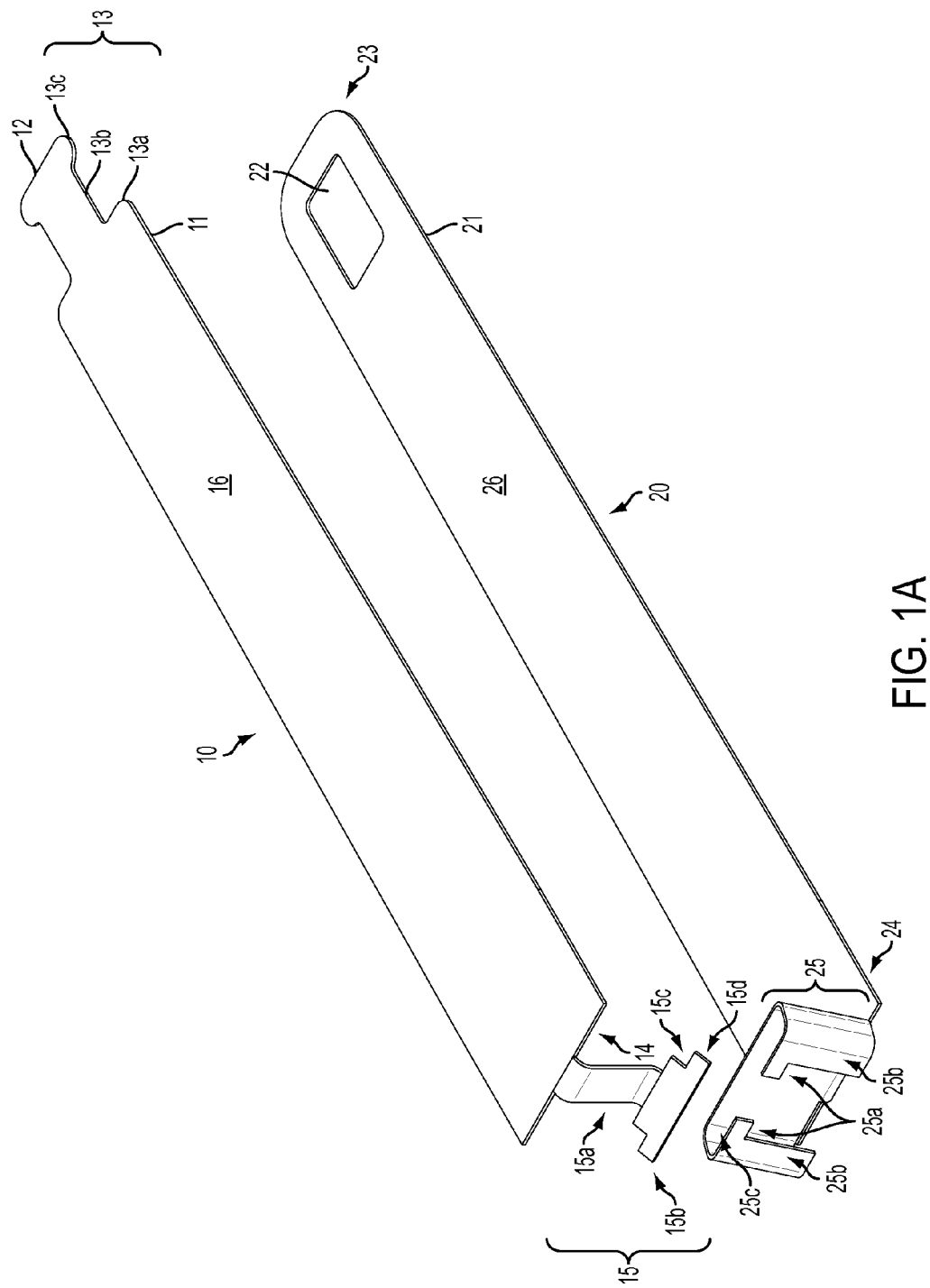
FIGS. 1A and 1B illustrate examples of a locking mechanism for a surgical instrument according to an exemplary embodiment.

First, the terms used in the present disclosure will be briefly described below before exemplary embodiments of the present inventive concept are described in greater detail.

Most of the terms used herein are general terms that have been widely used in the technical art to which the present inventive concept pertains. However, some of the terms used herein may be created reflecting intentions of technicians in this art, precedents, or new technologies. Also, some of the terms used herein may be arbitrarily chosen. In this case, these terms are defined in detail below. Accordingly, the specific terms used herein should be understood based on the unique meanings thereof and the whole context of the disclosure as set forth herein.

In the present specification, it should be understood that the terms, such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. Also, the terms, such as "portion" "piece," "section," "part," etc., should be understood as a part of a whole; an amount, section or piece. Further, as used herein, the term "and/or" includes any and all combinations of one or more of the associated listed items. Expressions such as "at least one of," when preceding a list of elements, modify the entire list of elements and do not modify the individual elements of the list.

Hereinafter, exemplary embodiments of the present invention will now be described more fully with reference to the accompanying drawings. The present inventive concept may, however, be embodied in many different forms and should not be construed as being limited to the exemplary embodiments set forth herein. Rather, these exemplary embodiments are provided so that this disclosure will be thorough and complete and will fully convey the concept of the invention to those of ordinary skill in the art. In the following description, well-known functions or constructions are not described in detail if it is determined that as they would obscure the disclosure due to explanation of the exemplary embodiments in unnecessary detail. The same reference numerals represent the same elements throughout the drawings.

FIG. 1A illustrates an example according to an exemplary embodiment. Flat parts 10 and 20 may be stamped from a piece of spring steel, or similar material. The term "stamped," "stamping," etc., as used herein, is used in a general sense and includes a variety of sheet-metal forming manufacturing processes, such as punching using a machine press or stamping press, coining, piercing, embossing, blanking, flanging, bending, etc., or some combination of such processes.

Again referring to FIG. 1A, a first flat part 10 is provided opposite a second flat part 20. The first flat part 10 is also referred to herein as a male side and the second flat part 20 is also referred to herein as a female side. The male side 10 has a distal end 11 which is nearest to the working end of the finished surgical tool (not shown), and a proximal end 14 which is opposite the distal end. Similarly, the female side 20 has distal and proximal ends 21 and 24, respectively. The distal end 11 of the male side 10 has a distal end extension 12, which may include a section 13 which is and the distal end 14 has a proximal end extension 16.

Again referring to FIG. 1A, the distal end 11 of the male side 10 may be stamped to form a particular shape, such as shown in FIG. 1A, including the I-shaped portion 13 having rounded corners 13a, a straight portion 13b and a tip portion 13c. The tip 13 may have a flat portion 12, which is formed to insert into and be securely coupled with another piece of the finished tool (not shown). Of course, other shapes are equally possible depending on the accommodated piece for the male side 10. Generally, the length and width of the pieces used to form the instrument will vary based on the desired instrument size, and will be proportionate to the finished instrument within a typical range of 20-35% of the size of the stamped pieces.

Similarly, referring again to FIG. 1A, the female side 20 may have a cutout portion 22 stamped into its distal end 21. The cutout portion 22 may accommodate so as to be securely coupled with another piece of the finished tool (not shown). The size and shape of the cut out portion 22 may vary depending on the size and shape of the accommodated piece of the finished tool. The exemplary embodiment shown in FIG. 1A includes rounded corners 23, but other shapes are equally possible depending on the accommodated piece. The pieces are then fitted together so as to form a counter-spring. It should be noted, however, that the locking mechanism may stand alone without the The proximal end 14 of the male side 10 may also be stamped so as to form a male extension 15 having a straight portion 15a and a graduated step portion 15b, as shown in FIG. 1A. The proximal end 24 of the female side 20 may also be stamped so as to form a female extension 25 having a pair of U-shaped portions 25b with a pair of protruding tabs 25a. Each of the U-shaped sections 25b may be substantially U-shaped meaning it may be formed to have rounded corners (not shown) or sectioned pieces such as shown in FIG. 1A. The pair of U-shaped sections may be formed so as to oppose one another to form a channel section 25c. The channel section 25c is formed so as to receive and accommodate the male extension 15. The graduated step portion 15b of the male extension 15 is shaped so as to catch on the pair of protruding tabs 25a of the female extension 25.

It should be noted that variations of the above-noted features are possible. For example, the angle of the straight portion 15a on the male side 10 (i.e., the angle being with respect to the top plane 26 of the male side 10) may be altered from that shown in FIG. 1A. Similarly, the angle of the channel section 25c on the female side 20 (i.e., the angle being with respect to the top plane 26 of the flat male side 10) may also be altered from that shown in FIG. 1A. Of course the respective angles of the straight portion 15a and the channel section 25c should be complementary so that the straight portion 15a is insertable into the channel section 25c from a free position, and then moveable to a locked position within the channel section 25c. Further, the angle between the graduated step portion 15b and the straight portion 15a may differ from that shown in FIG. 1A.

Another example of a variation may include a male extension having a tip which is shaped differently from the graduated step portion 15b described above. For example, the protruding tabs may have rounded corners.

Furthermore, it should be noted that the locking mechanism may stand alone without counter spring action. For example, the I-shaped portion 13 having rounded corners 13a, a straight portion 13b and a tip portion 13c and the corresponding cutout portion 22 may be omitted from the finished instrument.

Figure 2A:
FIGS. 2A-2F illustrate examples of a locking mechanism in a free state according to an exemplary embodiment.

FIG. 2A shows a side perspective view of the male side 10 and the female side 20 where the lock is in the free state, or free position. Hereinafter, the term "lock" refers to the combination of parts of which work together to create the locking mechanism, i.e., the male extension 15 and the female extension 25, as well as their respective component parts described hereinabove. The free state occurs when there is a gap G between the male extension 15 and the female extension 25, whereby the male side 10 and the female side 20 may be urged toward each other by a user in order to effect a motion at the working end of the surgical instrument (not shown). Alternatively, the working motion of the surgical instrument may require that one of the male side 10 and the female side 20 remain stationary while the other side is urged toward the stationary side.

FIG. 2A also shows the width W of the straight portion 15a of the male extension 15. The corresponding width W' of the space between the pair of protruding tabs 25a should be wide enough to accommodate the width W of the straight portion 15a, but not so wide as to prevent the pair of protruding tabs 25a from being able to catch and hold the male extension in the area of the graduated step portion 15b.

Further, while the protruding tabs 25a shown in FIG. 1A should be respectively wide enough so as to catch on the graduated step portion 15b, the protruding tabs 25a should also be formed so as to permit the outermost protruding tabs 15d of the graduated step portion 15b to catch on the front flat portions 25d of the U-shaped sections 25b. The left side of the female extension 25 has a left front flat portion 25d and the right side of the female extension 25 has a right front flat portion. That is, the relative size of space S, including the protruding tabs 25a, and the respective dimensions of the male extension 15 should collectively be formed so as to permit the innermost protruding tabs 15c of the graduated step portion 15b to fit within the space S, and at the same time, permit the outermost protruding tabs 15d to catch on the front flat portions 25d, as shown in FIG. 1B, thereby being able to hold the male extension 15 within the channel section 25c of the female extension 25.

Figure 1B:
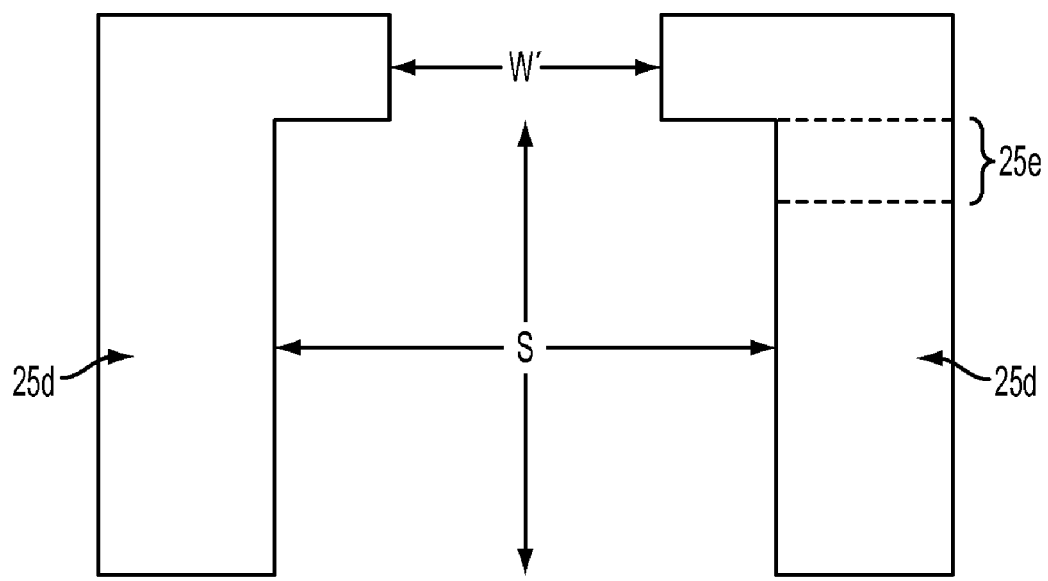

It should be noted that the front portions (i.e., the front flat portions) are not necessarily flat, and may be shaped differently so as to create a desired amount of opposing tension as the male extension 15 of the male side 10 is urged into the channel section 25c of the female side 20 beyond the area 25e constituting a locking position on the front flat portions 25d, as shown in FIG. 1B.

Figure 2B:
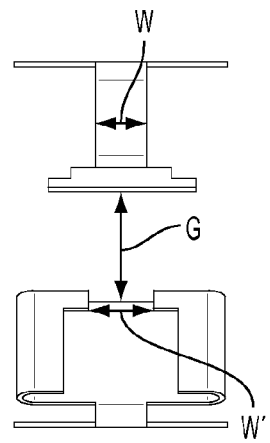

FIG. 2B shows a front perspective view of the lock in the free state. In FIG. 2B, the front side of the graduated step portion 15b can be seen with respect to the front side of the female extension 25. The pair of protruding tabs 25a can also be seen with respect to the gap G and the graduated step portion 15b, while the lock is in the free state.

Figure 2C:
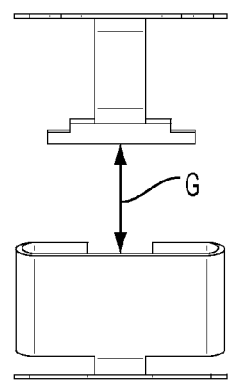
Figure 2D:
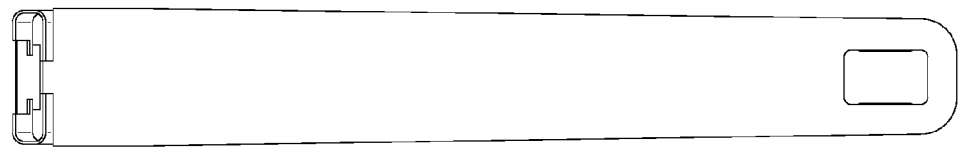
Figure 2E:
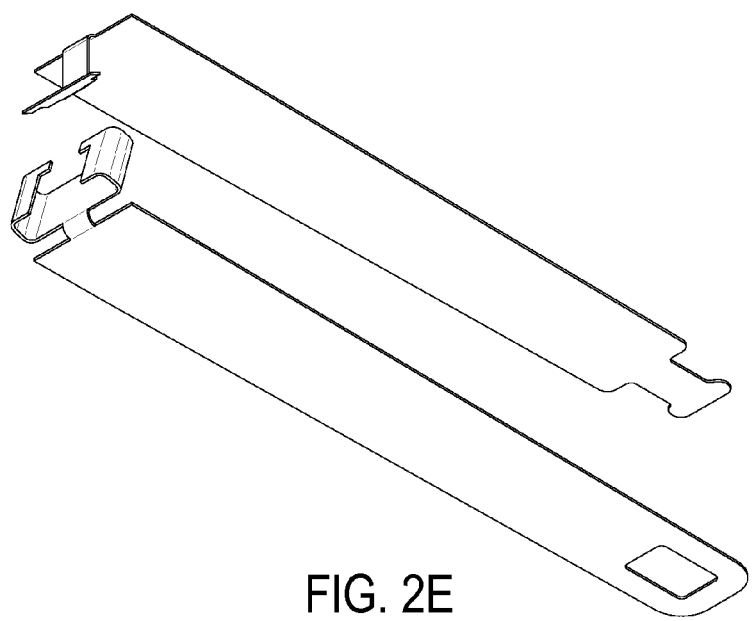
Figure 2F:
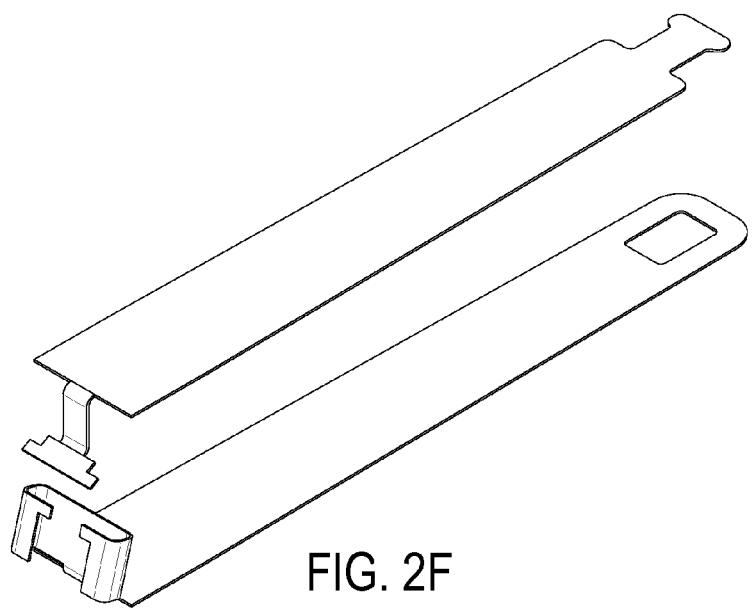

FIG. 2C shows a rear perspective view of the lock. The back side of the graduated step portion 15b can be seen with respect to the back side of the female extension 25. Again, the gap G is shown relative to the respective component parts of the lock. FIG. 2D shows a top perspective view, and FIGS. 2E and 2F offer perspective views from two different angles. In each case, the gap G can be seen between the male extension 15 and the female extension 25, when the lock is in the free state.

Figure 3A:
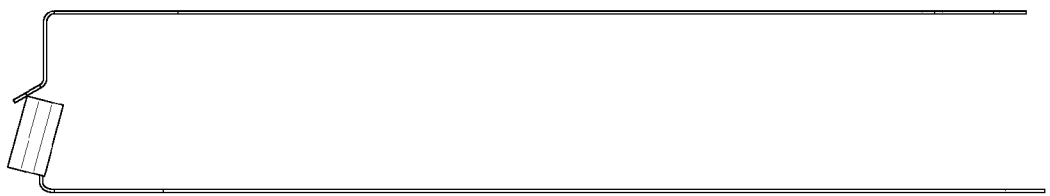
FIGS. 3A-3F illustrate examples of a locking mechanism in a position where the lock is touching but not yet locked according to an exemplary embodiment.
Figure 3B:
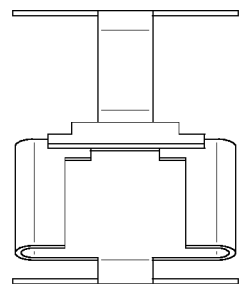
Figure 3C:
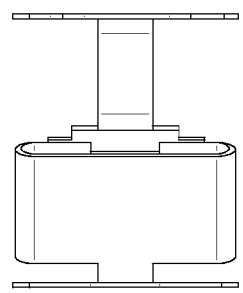
Figure 3D:
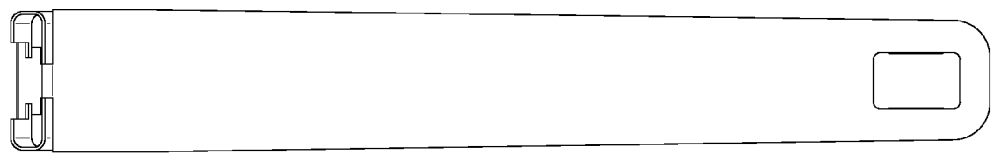
Figure 3E:
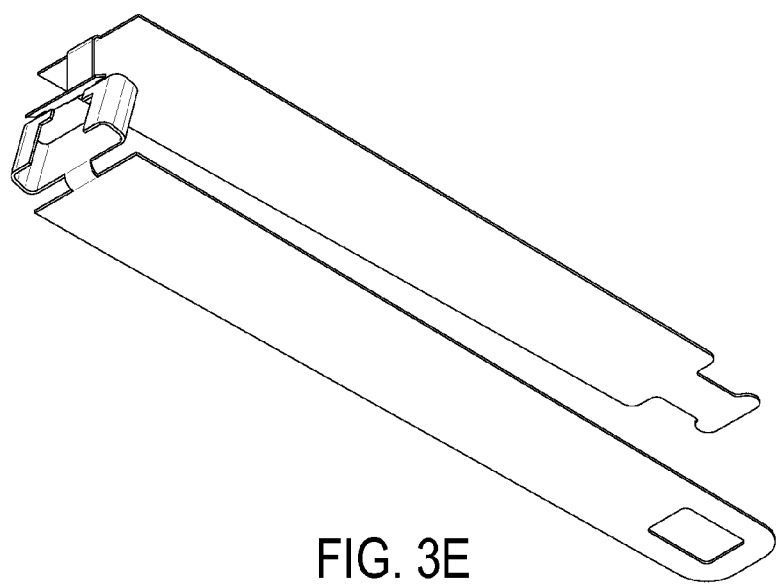
Figure 3F:
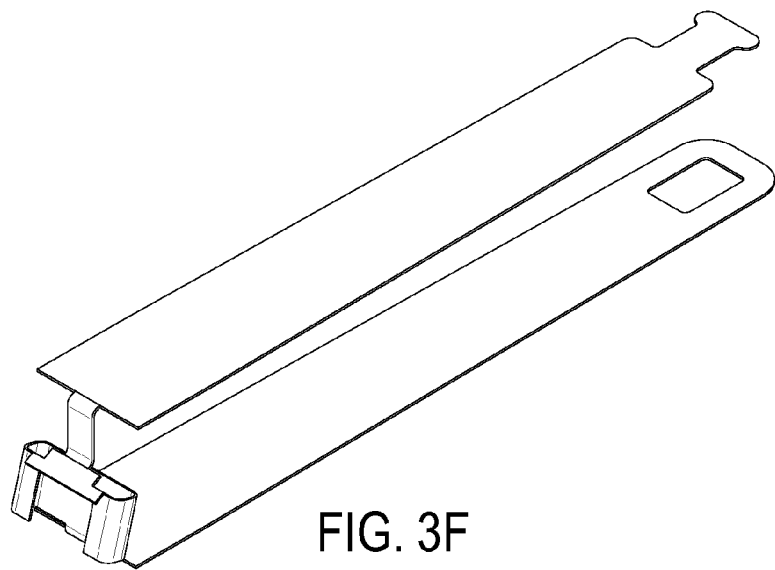

FIG. 3A shows a perspective view of the lock where, after urging one side or the other, or both, the male extension 15 is touching the female extension 25. Specifically, as shown in FIG. 3B, the male extension 15 is just touching the female extension 25, about to enter into the channel section 25c. This can also be seen from the various different perspective views shown in FIGS. 3C, 3D, 3E and 3F. Also, the gap G has diminished to effectively zero (i.e., a negligible amount). In this state, the lock is not yet locked, and as a result the tension applied by virtue of the connection of the male and female sides to the rest of the finished surgical instrument, the urged side(s) may tend to push back toward the free state.

It should be noted that the component parts of the male extension 15 (e.g., the straight portion 15a, the graduated step portion 15b, etc.), as well as the corresponding portions of the female extension 25, may be integrally formed or may be formed separately and coupled together so as to form a part which is consistent with the structural and functional considerations of the locking mechanism as discussed hereinabove.

Figure 4A:
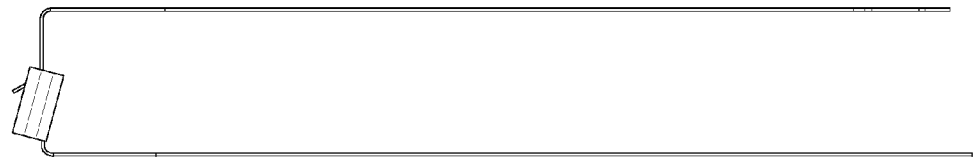
FIGS. 4A-4F illustrate examples of a locking mechanism in a position where the lock is locked according to an exemplary embodiment.

FIG. 4A shows an example of when the lock is locked. That is, the male side 10 has been urged toward the female side 20 beyond a predetermined distance. When this occurs, the straight portion 15a of the male extension 15 fits within the space W' between the protruding tabs 25a of the female extension 25, and the outermost pair of protruding tabs 15d of the graduated step portion 15b of the male extension 15 respectively contact the left and right front flat surfaces 25d of the female extension 25 in respective areas 25e on the and right front flat surfaces 25d of the female extension 25 and below the pair of protruding tabs 25a of the female extension 25.

Figure 4B:
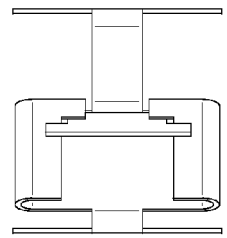
Figure 4C:
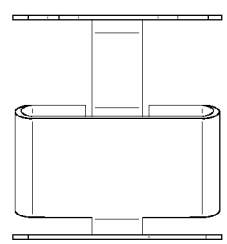
Figure 4D:
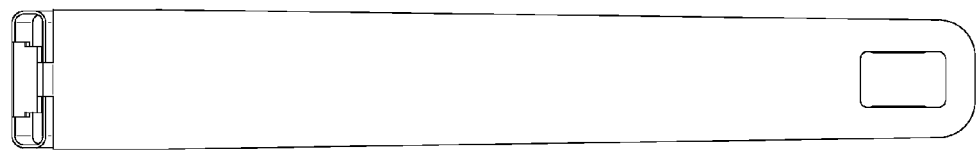

FIG. 4B shows a front perspective view of the lock in the locked state. FIG. 4C shows a rear perspective view of the lock in the locked state. FIG. 4D shows a top view of the lock in the locked state, and FIGS. 4E and 4F offer perspective views from two different angles.

Figure 4E:
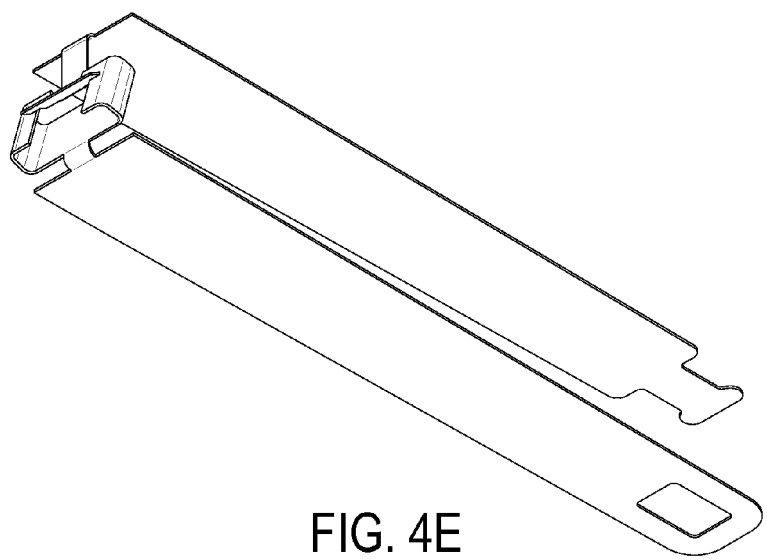
Figure 4F:
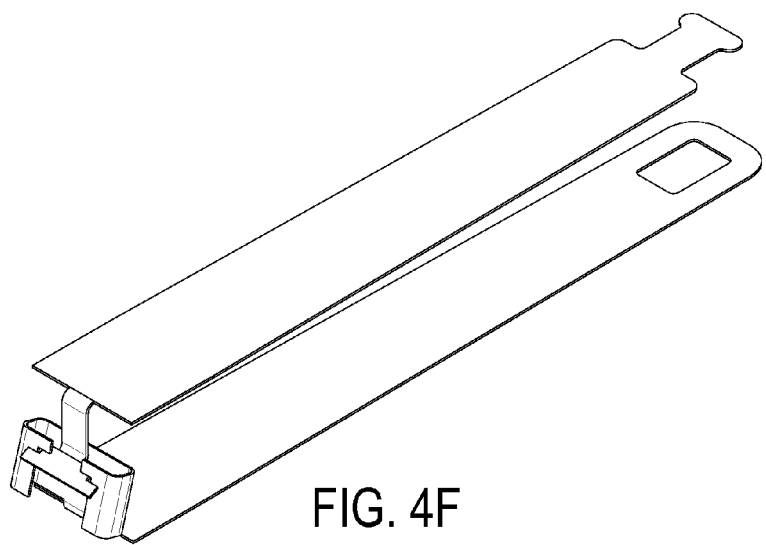

As shown in FIGS. 4E and 4F the graduated step portion 15b contacts the front flat surfaces 25d. Specifically, the outermost pair of protruding tabs 15d of the graduated step portion 15b of the male extension 15 respectively contact the left and right front flat surfaces 25d of the female extension 25 in respective areas 25e on the and right front flat surfaces 25d of the female extension 25 and below the pair of protruding tabs 25a of the female extension 25.

In FIGS. 4A-4C and FIGS. 4E and 4F, while in the locked state, in contrast to the situation when the lock is in the free state, it can be seen that there is no gap G between the male extension 15 and the female extension 25.

Figure 5A:
FIGS. 5A-5F illustrate examples of a locking mechanism in a position where the lock is released according to an exemplary embodiment.

FIG. 5A shows the situation where the male side 10 has been pushed past a predetermined distance (i.e., past a release point). The male extension 15 is sprung into the female extension 25 of the female side 20. That is, the channel section 25c is formed to accommodate the straight portion 15a, the innermost pair of protruding tabs 15c and the outermost pair of protruding tabs 15d of the graduated step portion 15c, as the male side 10 is urged toward the female side 20 beyond the second predetermined distance (i.e., the release point) and the locking mechanism moves from the locked state back to the free state.

Figure 5B:
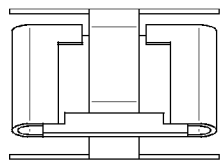
Figure 5C:
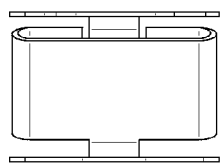
Figure 5D:
Figure 5E:
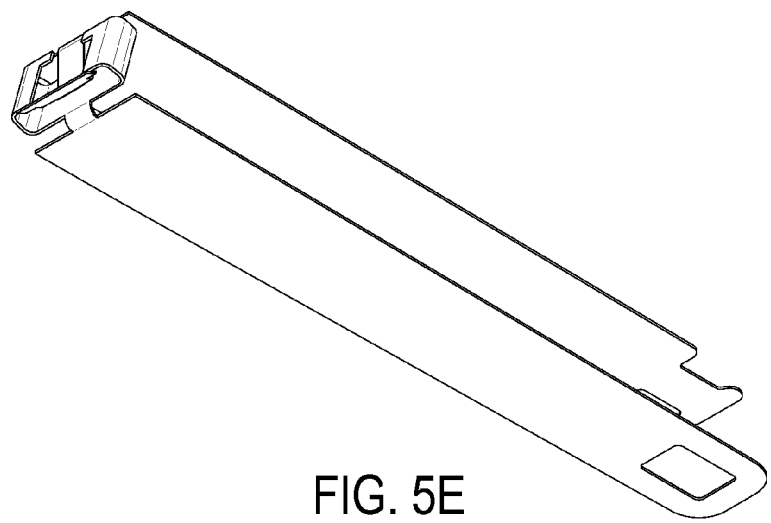
Figure 5F:
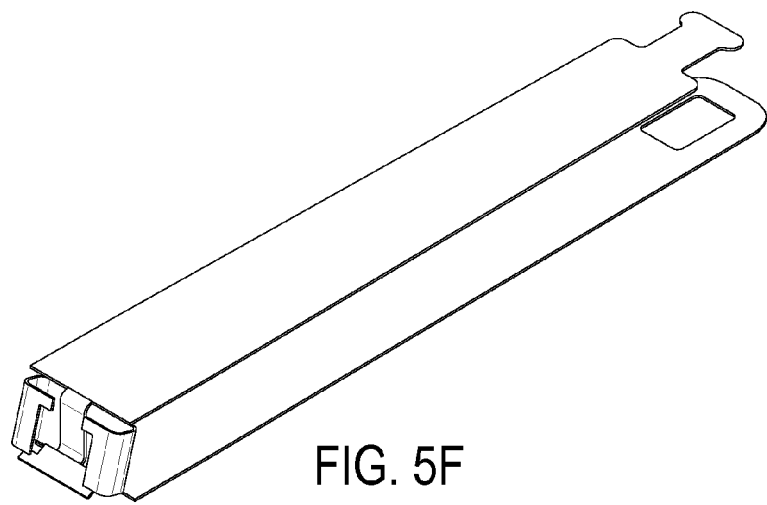

FIG. 5B shows a front perspective view which illustrates how the outermost pair of protruding tabs 15d are formed so as to fit within the channel section 25c if the male side 10 is urged toward the female side 20 beyond the release point. FIG. 5C shows a rear perspective view of the locking mechanism as the male side 10 is urged toward the female side 20 beyond the release point. FIG. 5D shows a top perspective view, and FIGS. 5E and 5F shown views from different angles when the locking mechanism as the male side 10 is urged toward the female side 20 beyond the release point.

FIGS. 6A-6F show the situation where the male extension 15 slides back through the female extension 25 as the male side 10 is urged toward the female side 20 beyond the release point, causing the locking mechanism to move from the locked state back to the free state.

Figure 6A:
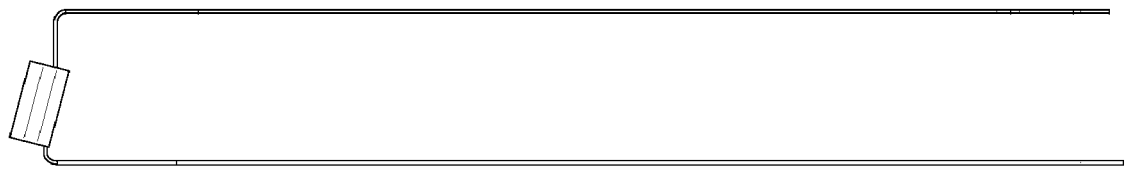
FIGS. 6A-6F illustrate examples of a locking mechanism in a position where the lock is released according to an exemplary embodiment.
Figure 6B:
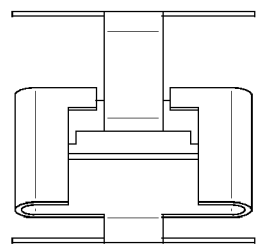

As shown in FIG. 6B, all of the components of the male extension 15 (i.e., the straight portion 15a and the graduated step portion 15b, including both the innermost pair of protruding tabs 15c and the outermost pair of protruding tabs 15d) fit within the channel section 25c formed by the opposing U-shaped sections of the 25b of the female extension 25. The whole male extension 15 is then guided within the channel section 25c of the female extension 25 so that the male side 10 is urged away from the female side 20 due to a spring force, thereby allowing the locking mechanism to move from the locked state back to the free state.

Figure 6C:
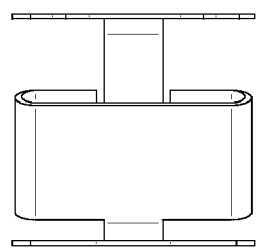
Figure 6D:
Figure 6E:
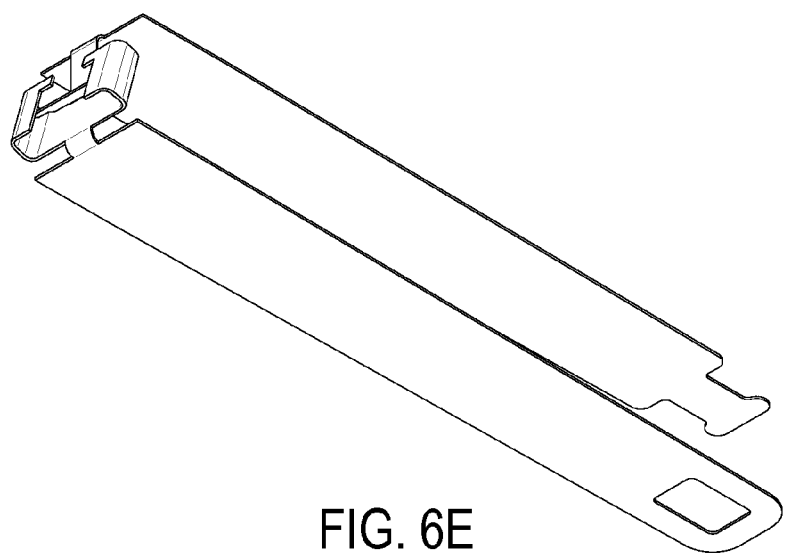
Figure 6F:
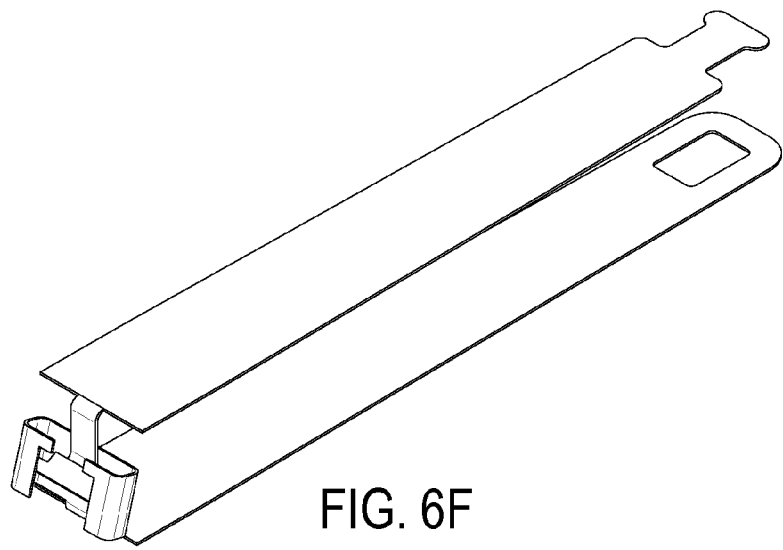

FIG. 6C shows a rear view, and FIG. 6D shows a top view the situation where the male extension 15 slides back through the female extension 25 as the male side 10 is urged toward the female side 20 beyond the release point, causing the locking mechanism to move from the locked state back to the free state. FIG. 6D shows how all of the components of the male extension 15 (i.e., the straight portion 15a and the graduated step portion 15b, including both the innermost pair of protruding tabs 15c and the outermost pair of protruding tabs 15d) fit within the channel section 25c formed by the opposing U-shaped sections of the 25b of the female extension 25. FIGS. 6E and 6F show different angles of the situation where the male extension 15 slides back through the female extension 25 as the male side 10 is urged toward the female side 20 beyond the release point, causing the locking mechanism to move from the locked state back to the free state.

Since all of the components of the male extension 15 (i.e., the straight portion 15a and the graduated step portion 15b, including both the innermost pair of protruding tabs 15c and the outermost pair of protruding tabs 15d) fit within the channel section 25c, the angle of the graduated step portion 15b of the male side 10 with respect to the straight portion 15a of the male side 10, may be formed so as to provide sufficient contact and friction between the male extension 15 and the channel section 25c of the female extension 25. For example, an application of the finished surgical instrument may require releasing the locking mechanism from the locked state at a desired rate. Alternatively, there may be no, or minimal contact between the male extension 15 and the channel section 25c of the female extension 25 as the male side 10 is urged beyond the release point and the male extension moves up through the channel section 25c.

The foregoing exemplary embodiments are merely exemplary and are not to be construed as limiting the present inventive concept. The exemplary embodiments can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A locking mechanism comprising:
a male extension including a straight portion and a graduated step portion; and
a female extension configured to receive the male extension, and including a pair of protruding tabs, which are spaced apart to allow the straight portion of the male extension to pass through a space between the protruding tabs, and which contact the graduated step portion if the male extension is inserted a first predetermined distance into the female extension;
wherein the graduated step portion of the male extension includes an outer pair of protruding tabs and an inner pair of protruding tabs,
the outer protruding tabs being configured to contact left and right front flat surfaces of the female extension if the male extension is inserted the first predetermined distance into the female extension; and
a top surface of each of the inner pair of protruding tabs of the graduated step portion of the male extension contacts a respective bottom surface of the pair of protruding tabs of the female extension if the male extension is inserted the first predetermined distance into the female extension.

2. The locking mechanism of claim 1, wherein the female extension further includes a pair of U-shaped sections which oppose each other.

3. The locking mechanism of claim 2, wherein upper portions of the pair of U-shaped sections respectively include the pair of protruding tabs, and
wherein lower portions of the pair of U-shaped sections respectively include the left and right front flat surfaces of the female extension.

4. The locking mechanism of claim 2, wherein the opposing U-shaped sections define a channel section into which the straight portion of the male extension is insertable.

5. The locking mechanism of claim 1, wherein the outer pair of protruding tabs respectively contact the left and right front flat surfaces of the female extension in respective areas on the left and right front flat surfaces of the female extension below the pair of protruding tabs of the female extension.

6. The locking mechanism of claim 1, wherein the inner pair of protruding tabs of the graduated step portion of the male extension fit within a space between the left and right front flat surfaces of the female extension and under the protruding tabs of the female extension.

7. The locking mechanism of claim 1, wherein if the male extension is inserted the first predetermined distance into the female extension, the locking mechanism is in a locked state where the male extension is prevented from moving away from the female extension.

8. The locking mechanism of claim 7, wherein if a gap exists between the male extension and the female extension, the locking mechanism is in a free state where the male extension is moveable in a direction away from the female extension.

9. The locking mechanism of claim 8, wherein if the male extension is urged toward the female extension a second predetermined distance beyond the first predetermined distance, the locking mechanism is moveable from the locked state to the free state.

10. The locking mechanism of claim 9, wherein the female extension further includes a pair of U-shaped sections which oppose each other, and the opposing U-shaped sections define a channel section into which the straight portion of the male extension is insertable as the male extension is urged toward the female extension moving from the free state to the locked state.

11. The locking mechanism of claim 10,
wherein the channel section accommodates the outer pair of protruding tabs of the graduated step portion as the male extension is urged toward the female extension beyond the second predetermined distance and the locking mechanism moves from the locked state back to the free state.

12. An instrument, comprising
a first handle portion,
a second handle portion, and
the locking mechanism of claim 1,
wherein the male extension is connected to the first handle portion and the female extension is connected to the second handle portion.

13. The instrument of claim 12, wherein the instrument is a surgical instrument having a proximal end and a distal end, the proximal end being toward a working portion of the surgical instrument, and the distal end being further away from the working portion of the surgical instrument than the proximal end.

14. The instrument of claim 13, wherein the locking mechanism is located closer to the distal end than the proximal end of the surgical instrument.

15. The instrument of claim 13, wherein the surgical instrument is a pair of forceps.

16. The instrument of claim 13, wherein the surgical instrument is a pair of surgical scissors.

17. The locking mechanism of claim 1, wherein if the male extension is urged toward the female extension a second predetermined distance beyond the first predetermined distance such that the inner pair of protruding tabs of the graduated step portion of the male extension is moved beyond the bottom surface of the pair of protruding tabs of the female extension, the locking mechanism is moveable from a locked state to a free state.

18. The locking mechanism of claim 1, wherein the outer protruding tabs comprise outermost protruding tabs and the inner protruding tabs comprise innermost protruding tabs.

* * * * *